Figure 1:
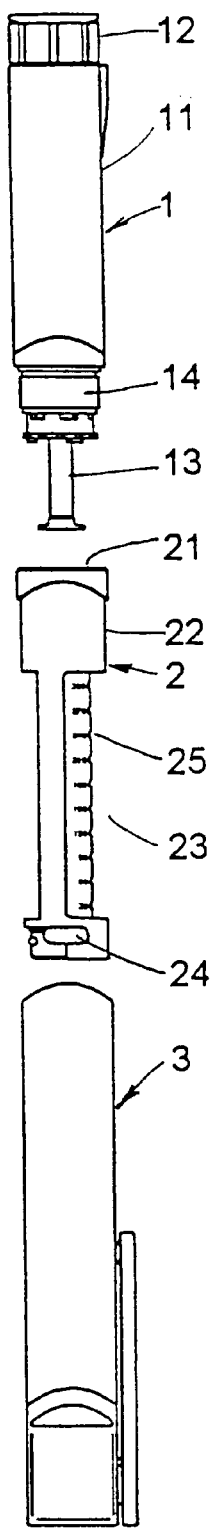

United States Patent [19]
Hansen

[11] Patent Number: 5,980,491
[45] Date of Patent: Nov. 9, 1999

[54] AUTOMATIC NEEDLE INSERTION MECHANISM

[75] Inventor: Niels-Aage Hansen, Havdrup, Denmark

[73] Assignee: Novo Nordisk A/S, Bagsvaerd, Denmark

[21] Appl. No.: 08/887,871

[22] Filed: Jul. 3, 1997

[30] Foreign Application Priority Data

Jul. 5, 1996 [DK] Denmark ................................. 0751/96

[51] Int. Cl.⁶ ..................................................... A61M 5/20
[52] U.S. Cl. ........................................... 604/157; 604/137
[58] Field of Search ................................... 604/117, 156, 604/157, 134–138, 207, 211

[56] References Cited

U.S. PATENT DOCUMENTS

| | | | |
|---|---|---|---|
| 4,850,973 | 7/1989 | Jordan et al. . | |
| 5,141,496 | 8/1992 | Dalto et al. . | |
| 5,282,793 | 2/1994 | Larson . | |
| 5,358,489 | 10/1994 | Wyrick ..................................... | 604/136 |
| 5,478,316 | 12/1995 | Bitdinger et al. ........................ | 604/135 |
| 5,591,188 | 1/1997 | Wasman .................................... | 606/182 |
| 5,634,906 | 6/1997 | Haber et al. .............................. | 604/136 |
| 5,637,094 | 6/1997 | Stewart, Jr. et al. .................... | 604/135 |

FOREIGN PATENT DOCUMENTS 0 388 169 A2  9/1990  European Pat. Off. .

*Primary Examiner*—Wynn Wood Coggins
*Assistant Examiner*—Deborah Blyveis
*Attorney, Agent, or Firm*—Steve T. Zelson, Esq.

[57] ABSTRACT

An automatic needle insertion device for a pen shaped syringe comprising a cartridge holder (2) wherein a cartridge with a drug can be accommodated, and a dose setting and injection part (1) by which a wanted dose may be set an subsequently pressed out from the cartridge by pressing a button (12) projecting from the dose setting and injection part (1). The device comprises a mainly tubular housing (31) in which a tubular pen holder (22) in which a pen can be mounted can be axially displaced in a proximal direction to cock a spring (30) which can thereafter be released to drive the pen holder (22) with the pen a set distance in a distal direction.

4 Claims, 2 Drawing Sheets

AUTOMATIC NEEDLE INSERTION MECHANISM

This application is claims priority under 35 U.S.C. 119 of Danish application serial no. 0751/96 filed Jul. 5, 1996, the contents of which are fully incorporated herein by reference.

The invention relates to automatic needle insertion mechanisms for pen shaped syringes comprising a cartridge holder wherein a cartridge with a drug can be accommodated, and a dose setting and injection part by which a wanted dose may be set and subsequently pressed out from the cartridge by pressing a button projecting from the dose setting and injection part. As it will be understood the dose setting and injection part forms the more mechanically complicated part of the syringe whereas the cartridge holder is a rather simple tubular part. The designation "pen shaped" shall be taken broadly recognising that a pen need not be oblong and have a circular cross section. Syringes designed to apportion a number of set doses from an ampoule and commonly carried by the user are often called pens even when they do not have a shape making them look like a fountain pen as had the first syringes of that kind.

Pen syringes are mainly used by patients to perform self injections. By such handling by non professionals it is important that the handling is simple so that complications are avoided. A phase of the injection upon which most people look at with disinclination is the needle insertion phase. This disinclination may incur that the needle insertion is not performed as purposefully quickly as it is appropriate to obtain a precise, uncomplicated and painless insertion.

Consequently different apparatus for automatic needle insertion has been proposed. U.S. Pat. No. 4,787,891 describes an injection apparatus for common single dose syringes. In this apparatus the syringe is mounted in a holder which against the force of a spring may be drawn into a barrel and locked in its retracted position. When the barrel is placed where the needle insertion is wanted and the lock is released, the holder with the syringe is forced forwards by the spring and a needle mounted on the syringe will project from the end of the barrel and pierce the skin where the barrel is placed.

From WO 88/08725 a pen shaped syringe is known wherein an automatic needle insert mechanism is integrated. The spring which provides the force necessary to insert the needle is further used to inject a set doe of medicine from the ampoule in the pen syringe. However, users may prefer to perform the injection themselves as this offers a possibility of adjusting the injection speed in accordance with the receiving ability of the tissue so that tensions and infiltrations are avoided.

Also pen shaped syringes with integrated needle insertion mechanisms but without automatic injection are known. Consequently, it is possible to buy pen syringes with built in needle insertion mechanisms.

If one has a pen syringe without such a mechanism, it will be attractive to have a separate needle insertion mechanism in which a pen shaped syringe may be mounted. This will give the user a freedom to the extent he may want to sometimes use a pen with and sometimes a pen without an automatic needle insertion mechanism.

The object of the invention is to provide such an automatic needle insertion mechanism for a syringes by which more individually set doses may be apportioned from a cylinder ampoule which can be changed when empty.

This is obtained by a pen shaped syringe of the kind described in the opening of this application, which syringe is according to the invention characterised in that the device comprises a mainly tubular housing in which a tubular pen holder in which a pen can be mounted can be axially displaced in a proximal direction to cock a spring which can thereafter be released to drive the pen holder with the pen a set distance in a distal direction. It shall be noticed that the designation "tubular" do not necessarily involve a tube having a circular cross section, the tube may have any appropriate cross section, e.g. a rectangular cross section.

In an appropriate embodiment of the invention the pen holder is shaped as a cartridge holder and only the dose setting and injection part of the pen syringe is mounted in the pen holder.

The cartridge holder forms a simple and inexpensive part of the pen syringe which part is designed to be in a simple way dismounted from the syringe when a new cartridge is going to be mounted. A cartridge holder with an automatic needle insertion mechanism can be seen as a spare part which can replace the common cartridge holder. If later a syringe without auto insertion device is wanted, the cartridge holder may again be replaced by the original simple one.

In a further appropriate embodiment of the mechanism according to the invention the cartridge holder shaped pen holder may at a proximal end have an inner thread in which an outer thread of the dose setting and injection part of a pen may be received.

According to the invention the pen holder may be provided with inspection windows to allow the same inspections as do a common cartridge holder. This way confusion of a user who is familiar with the pen with the original cartridge holder is avoided. It is an advantage that the means for operating the needle insertion device are firmly connected with the pen holder so that no superfluous operating means are left on the pen syringe when the pen holder with the automatic needle insertion device is replaced by the original cartridge holder.

According to an embodiment of the invention the distal end of the tubular housing of the automatic needle insertion device may be obliquely cut to allow abutment against the skin at an angle so that the needle may be inserted at an angle of about 45°.

Figure 2:
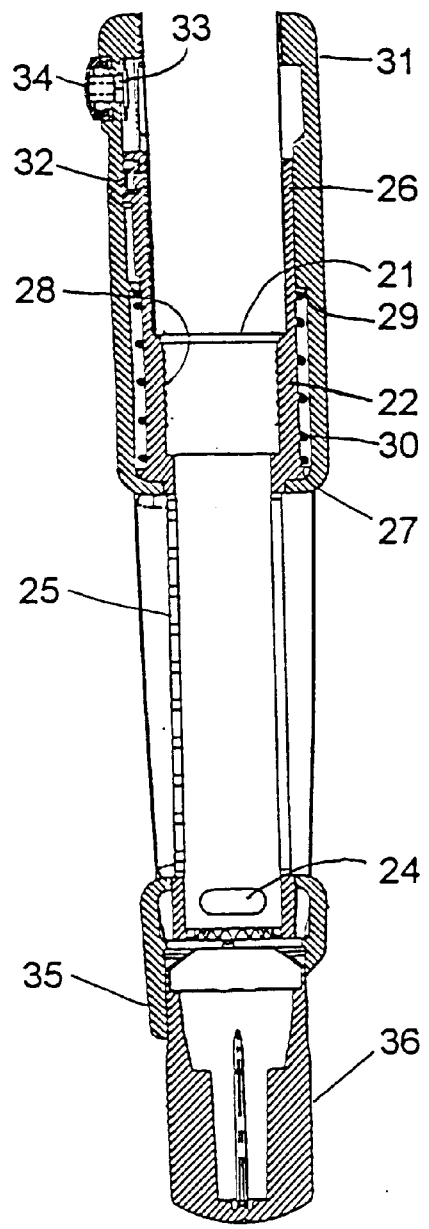

In the following the needle insertion mechanism according to the invention will be described with reference to the drawing, wherein FIG. 1 shows a common known pen shaped syringe for the delivery set doses of medicine from a cartridge, FIG. 2 shows a sectional view of an automatic needle insertion device with a cartridge holder shaped pen holder.

Figure 3:
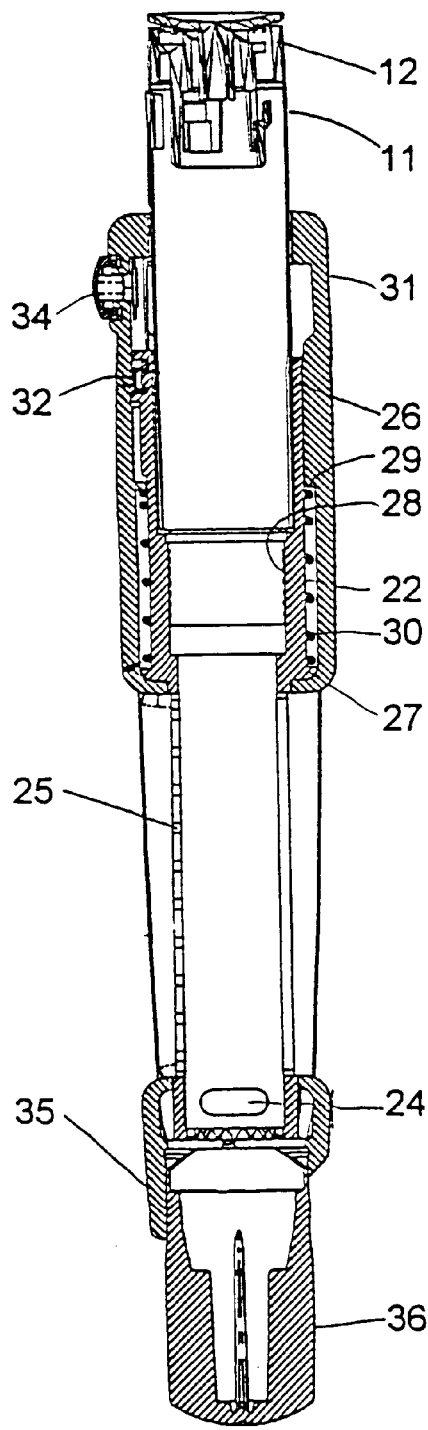
Figure 4:
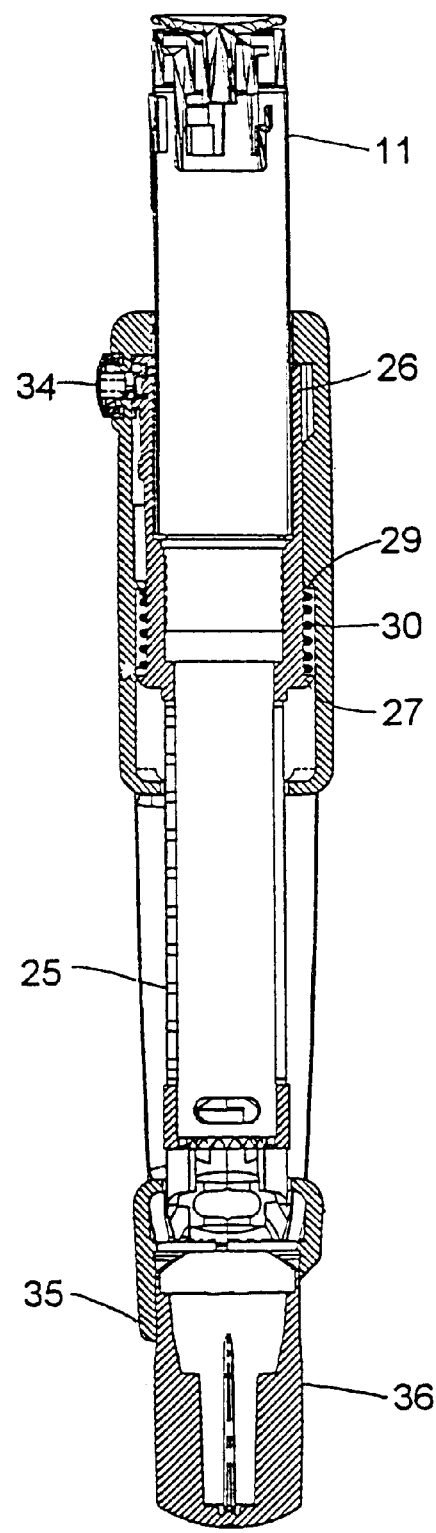

FIG. 3 shows a pen shaped syringe mounted with the pen holder shown in FIG. 2, with the needle insertion mechanism uncocked, and FIG. 4 the device in FIG. 3 with the needle insertion mechanism cocked.

FIG. 1 shows schematically a pen shaped syringe for injection of set doses of medicine from a cartridge. The syringe consists of a dose setting part 1 comprising a housing containing a dose setting mechanism in which an intended dose may be set by turning a dose setting knob 12. During the setting of the dose the knob 12 is elevated from the housing 11 a distance proportional with the size of the dose set. When the knob 12 is pressed back to abutment with the housing, a piston rod 13 extending from the housing will be driven further out from the end of the housing opposite the knob 12 another distance proportional with the set dose. An external thread 14 at the end of the housing from which the piston rod projects serves the connection of said housing with a cartridge holder 2.

The cartridge holder 2 has at an end 21 an internal thread for the receipt of the external thread 14 of the dose setting part 1. The cartridge holder 2 has a tubular body 22 wherein a cartridge of the kind which is at an output end closed by a rubber membrane and at the other end closed by a piston may be accommodated with its piston facing the end 21 of the cartridge holder 2. Cut-outs 23 in the wall of the body enables inspection of the not shown cartridge mounted in the holder. The remaining wall of the body is provided with marks 25 indicating how much medicine is left in the cartridge when the piston reach the respective marks. A further inspection window 24 near the end of the cartridge makes it possible to inspect the output end of the cartridge to see whether the cartridge is emptied to an extent that calls for a change of said cartridge.

A cap 3 can cover the cartridge holder and a possible injection needle mounted at the output end of the cartridge so that the pen may be kept free from dust and the needle is protected.

FIG. 2 shows a sectional view of a cartridge holder into which a needle insertion mechanism is integrated. Details corresponding to details in the cartridge holder 2 shown in FIG. 1 is given the same reference numbers. This goes for the body 22 which however is supplied with an elongation 26 and a collar 27, the marks 25, the inspection window 24 and the end 21 in which further an internal thread 28 is seen.

The cartridge holder body is enclosed by two shells which are joined together along their edges to form a housing 31 in which the cartridge holder body is mounted axially displaceable. Between an inward projection 29 in the housing and the collar 27 surrounding the cartridge holder body a helical spring 30 is mounted surrounding the end of the cartridge holder which carries the internal thread 22 for reception of a dose setting part 1. When the cartridge holder body 22 with its elongation is drawn upwards in the housing 31 in FIG. 2, the helical spring is compressed and when the body is drawn so far that a spring ring 32 can engage an opening 33 near the upper end of the housing, the cartridge holder body will be held in a cocked position from which it may be released by pressing a trigger button 34 at the upper end of the housing 31.

One of the shells forming the housing has at its lower end in FIG. 2 a rest piece 35 which may be placed resting against the skin where an injection is going to be made whereas the lower end of the other shell is without such a rest so that an opening between the skin and the end of the housing is formed for inspection of the needle in its position ready for insertion perpendicularly to the skin. Alternatively the fact that the resting piece lacks on one of the shells allows that the syringe is held with the rest piece of one shell and the edge of the shell which has no rest piece in abutment with the skin so that the needle pierces the skin at an angle of about 45°. The lower end of the housing is closed by a protective cap 36 when the device is not in use.

FIG. 3 shows a dose setting part 1 of a pen shaped syringe mounted with a cartridge holder wherein a needle insertion mechanism is integrated. The dose setting part 1 has its external thread 14 screwed into the internal thread 28 of the cartridge holder. The dose setting part which project over the end of the cartridge holder housing forms a good grip by which the cartridge holder body 22 may be drawn upwards in the housing in FIG. 3 to compress the spring 30 between the collar 27 of the cartridge holder body and the inward projection 29 of the housing 31. In the uncocked condition of the device the needle will project beyond the rest piece 35 whereas the needle in the cocked condition of the device as shown in FIG. 4 will be retracted a short distance behind the outer end of the rest piece.

I claim:

1. An automatic needle insertion device for a pen-shaped syringe of the type including a cartridge holder for containing a cartridge with a drug to be administered, and a dose-setting and injection part by which a desired dose can be set and subsequently injected, said device comprising:

a mainly tubular housing having proximal and distal ends, and including a rest portion at said distal end which can be placed against the skin;

a cartridge holder mounted in said tubular housing so as to be axial displaceable, wherein the cartridge holder includes a distal end with a needle mount for receiving an injection needle, and a proximal end for receiving a dose-setting and injection part;

a spring mounted in said tubular housing and engaging, at opposite ends, said tubular housing and said cartridge holder such that moving said cartridge holder in said proximal direction, relative to said tubular housing, cocks said spring;

wherein said cartridge holder is axially moveable between an injection position, in which a needle mounted thereon projects in a distal direction from said rest portion by a predetermined distance, and a cocked position, in which a needle mounted thereon lies a proximal distance from said rest portion, whereby an injection can be administered by mounting a cartridge in, and a dose-setting and injection mechanism and an injection needle on, said cartridge holder; moving said cartridge holder, and with it said dose-setting and injection mechanism and needle, to said cocked position, thereby cocking said spring; placing said rest portion against the skin at the desired injection location, and releasing said spring to cause said needle to penetrate the skin by the predetermined distance; and finally injecting a predetermined dose using said dose-setting and injection mechanism.

2. A device according to claim 1, wherein said cartridge holder has an inner thread at said proximal end for receiving a corresponding outer thread on a dose-setting and injection mechanism of a pen shaped syringe.

3. A device according to claim 2, wherein said cartridge holder has at least one inspection window allowing visual inspection of a cartridge as in the case of a conventional cartridge holder of a pen-shaped syringe.

4. A device according to claim 2, wherein said rest portion is obliquely cut so that the needle pierces the skin at an angle.

* * * * *